United States Patent [19]

Coy

[11] Patent Number: 4,647,653

[45] Date of Patent: Mar. 3, 1987

[54] THERAPEUTIC PEPTIDES

[75] Inventor: David H. Coy, New Orleans, La.

[73] Assignee: Tulane Educational Fund, New Orleans, La.

[21] Appl. No.: 643,643

[22] Filed: Aug. 23, 1984

[51] Int. Cl.$^4$ ............................................. C07K 7/20
[52] U.S. Cl. ................................................... 530/313
[58] Field of Search ............... 260/112.5 LH; 530/313

[56] References Cited

U.S. PATENT DOCUMENTS

| 4,075,191 | 2/1978 | Beddell et al. | 260/112.5 LH |
| 4,317,815 | 3/1982 | Coy | 260/112.5 LH |
| 4,431,635 | 2/1984 | Coy | 260/112.5 LH |
| 4,444,759 | 4/1984 | Rivier et al. | 260/112.5 LH |

FOREIGN PATENT DOCUMENTS 0097031 12/1983 European Pat. Off. .

OTHER PUBLICATIONS

*Chemical Abstracts*, 103, 74 (1985), Abst. No. 775b.

Primary Examiner—Delbert R. Phillips

[57] ABSTRACT

A decapeptide of the formula: Ac-$A^1$-$A^2$-D-Trp-Ser-Tyr-$A^3$-$A^4$-$A^5$-$A^6$-$A^7$-$NH_2$ wherein each $A^1$ and $A^2$, independently, is D-Trp, D-$\beta$-Nal, or D-p-X-Phe, wherein X is a halogen or $CH_3$; $A^3$ is D-$\beta$-Nal, D-Trp, D-Lys, D-Arg, D-homo-Arg, D-diethyl-homo-Arg, or D-p-X-Phe, wherein X is a halogen or $CH_3$; $A^4$ is Phe, Tyr, pentafluoro-Phe, Trp, $\beta$-Nal, or p-X-Phe, wherein X is a halogen or $CH_3$; $A^5$ is Arg or Lys; $A^6$ is Pro or hydroxy-Pro; and $A^7$ is Gly or D-Ala; or a pharmaceutically acceptable salt thereof.

13 Claims, No Drawings

THERAPEUTIC PEPTIDES

BACKGROUND OF THE INVENTION

This invention relates to therapeutic peptides.

A number of luteinizing hormone releasing hormone (LH-RH) analogs have been described which inhibit the release of LH-RH, a peptide hormone having the formula pGlu-His-Trp-Ser-Tyr-Gly-Leu-Arg-Pro-Gly-NH$_2$. For example, Coy et al. U.S. Pat. No. 4,431,635, hereby incorporated by reference, describes LH-RH analogs having the general formula X-R$^1$-R$^2$-R$^3$-Ser-Tyr-R$^4$-Leu-Arg-Pro-R$^5$-NH$_2$, in which X can be Acetyl (AC); R$^1$ and R$^4$, independently, can be D-Trp or D-p-X-Phe, where X is a halogen or methyl group and (represents such throughout the rest of this application); R$^2$ can be D-p-X-Phe; R$^3$ can be D-Trp; and R$^{10}$ can be Gly or D-Ala.

SUMMARY OF THE INVENTION

In general, the invention features a decapeptide of the formula:

Ac-A$^1$-A$^2$-D-Trp-Ser-Tyr-A$^3$-A$^4$-A$^5$-A$^6$-A$^7$-NH$_2$ wherein each A$^1$ and A$^2$, independently, is D-Trp, D-β-Nal, or D-p-X-Phe, wherein X is a halogen or CH$_3$; A$^3$ is D-β-Nal, D-Trp, D-Lys, D-Arg, D-homo-Arg, D-diethyl-homo-Arg, or D-p-X-Phe, wherein X is a halogen or CH$_3$; A$^4$ is Phe, Tyr, pentafluoro-Phe, Trp, β-Nal, or p-X-Phe, wherein X is a halogen or CH$_3$; A$^5$ is Arg or Lys; A$^6$ is Pro or hydroxy-Pro; and A$^7$ is Gly or D-Ala; or a pharmaceutically acceptable salt thereof.

In preferred embodiments of the decapeptide, A$^1$ is D-β-Nal; A$^2$ is D-p-Cl-Phe; A$^3$ is D-Arg; A$^5$ is Arg; and A$^7$ is D-Ala; or a pharmaceutically acceptable salt thereof. Specific compounds include (giving the formulae in terms of modifications of LH-RH at numbered positions): Ac-[D-β-Nal-1, D-p-Cl-Phe-2, D-Trp-3, D-Arg-6, Phe-7, D-Ala-10]-LH-RH; Ac-[D-β-Nal-1, D-p-Cl-Phe-2, D-Trp-3, D-Arg-6, Tyr-7, D-Ala-10]-LH-RH; Ac-[D-β-Nal-1, D-p-Cl-Phe-2, D-Trp-3, D-Arg-6, p-Cl-Phe-7, D-Ala-10]-LH-RH; Ac-[D-β-Nal-1, D-p-Cl-Phe-2, D-Trp-3, D-Arg-6, p-F-Phe-7, D-Ala-10]-LH-RH; Ac-[D-β-Nal-1, D-p-Cl-Phe-2, D-Trp-3, D-Arg-6, p-Me-Phe-7, D-Ala-10]-LH-RH; Ac-[D-β-Nal-1, D-p-Cl-Phe-2, D-Trp-3, D-Arg-6, pentafluoro-Phe-7, D-Ala-10]-LH-RH; Ac-[D-β-Nal-1, D-p-Cl-Phe-2, D-Trp-3, D-Arg-6, Trp-7, D-Ala-10]-LH-RH; Ac-[D-β-Nal-1, D-p-Cl-Phe-2, D-Trp-3, D-Arg-6, β-Nal-7, D-Ala-10]-LH-RH; Ac-[D-β-Nal-1, D-p-Cl-Phe-2, D-Trp-3, D-Arg-6, Phe-7, hydroxy-Pro-9, D-Ala-10]-LH-RH; Ac-[D-β-Nal-1, D-p-Cl-Phe-2, D-Lys-6, Phe-7, D-Ala-10]-LH-RH; and Ac-[D-p-Cl-Phe-1, D-p-Cl-Phe-2, D-Trp-3, D-Arg-6, Phe-7, D-Ala-10]-LH-RH; or pharmaceutically acceptable salts thereof.

In other preferred embodiments, a therapeutically effective amount of the therapeutic decapeptide and a pharmaceutically acceptable carrier substance, e.g., magnesium carbonate or lactose, together form a therapeutic composition for inhibiting the release of LH-RH. This composition can be in the form of a pill, tablet, capsule, liquid, or sustained release tablet for oral administration; a liquid for nasal administration; or a liquid for intravenous, subcutaneous, parenteral, or intraperitoneal administration.

The decapeptides of the invention are active in inhibiting the release of LH-RH and exhibit a long duration of activity, thus minimizing the amount and frequency of dosages. Furthermore, manufacture is relatively simple and inexpensive.

Other features and advantages of the invention will be apparent from the following description of the preferred embodiments thereof, and from the claims.

DESCRIPTION OF THE PREFERRED EMBODIMENTS

We now describe the structure, synthesis, and use of preferred embodiments of the invention.

Structure

The decapeptides of the invention have the general formula recited in the Summary of the Invention above. They all have an acetyl group at the amino terminal end and an NH$_2$ at the carboxy terminal end, in addition to D-Trp at position 3, Ser at position 4, and Tyr at position 5.

The decapeptides can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

Synthesis

The synthesis of N-Ac-D-β-Nal-D-p-Cl-Phe-D-Trp-Ser-Tyr-D-Arg-Phe-Arg-Pro-D-Ala-NH$_2$ follows.

Other decapeptides of the invention can be prepared by making appropriate modifications of the following synthetic method.

The first step is the preparation of N-acetyl-D-β-Nal-D-p-Cl-Phe-D-Trp-O-benzyl-Ser-Tyr-D-tosyl-Arg-Phe-tosyl-Arg-Pro-D-Ala -benzyhydrylamine-resin, as follows.

Benzyhydrylamine-polystyrene resin (Bachem, Inc.) (1.00 g, 0.3 mmole) in the chloride ion form is placed in the reaction vessel of a Beckman 990B peptide synthesizer programmed to perform the following reaction cycle: (a) CH$_2$Cl$_2$; (b) 33% trifluoroacetic acid in CH$_2$Cl$_2$; (2 times for 1 and 25 min each); (c) CH$_2$Cl$_2$; (d) ethanol; (e) CH$_2$Cl$_2$; (f) 10% triethylamine in CHCl$_3$; and (g) CH$_2$Cl$_2$.

The neutralized resin is stirred with alpha-t-butoxycarbonyl (Boc)-D-Ala and diisopropylcarbodiimide (1.5 mmole) in CH$_2$Cl$_2$ for 1 hour and the resulting amino acid resin is then cycled through steps (a) to (g) in the above wash program. The following amino acids (1.5 mmole) are then coupled successively by the same procedure: Boc-Pro, Boc-Tosyl-Arg, Boc-Phe, Boc-Tosyl-D-Arg, Boc-Tyr, Boc-benzyl-Ser, Boc-D-Trp, Boc-D-p-Cl-Phe, and Boc-D-β-Nal.

After removal of the N-terminal Boc group, the peptide-benzyhydrylamine resin is neutralized and acetylated by treatment with 5% acetic acid in CH$_2$Cl$_2$. The completed resin is then washed with CH$_3$OH and air dried.

From the above resin is prepared N-Ac-D-β-Nal-D-p-Cl-Phe-D-Trp-Ser-Tyr-D-Arg-Phe-Arg-Pro-D-Ala-NH$_2$, as follows.

A mixture of the above decapeptide resin (1.85 g, 0.5 mmole) and a solution of 4 ml anisole, 100 mg dithiothreitol, and 36 ml hydrogen fluoride is stirred at 0° C. for 45 minutes. Excess hydrogen fluoride is evaporated rapidly under a stream of dry nitrogen, after which the free peptide is precipitated and washed with ether.

The peptide is then dissolved in a minimum volume of 50% acetic acid and eluted on a column (2.5×100 mm) of Sephadex G-25. Fractions containing a major component, as determined by u.v. absorption and thin layer chromatography (tlc) are pooled and evaporated to a small volume in vacuo. This solution is applied to a column (2.5×50 cm) of octadecylsilane-silica (Whatman LRP-1, 15-20 um mesh size) which is eluted with a linear gradient of 15-50% acetonitrile in 20% acetic acid in water. Fractions are examined by tlc and analytical high performance liquid chromatography (hplc) and pooled to give maximum purity. Repeated lyophilization of the solution from water gives 117 mg of the product as a white, fluffy powder.

This material is found to be homogeneous by hplc and tlc. Amino acid analysis of an acid hydrolysate confirms the composition of the decapeptide.

Ac-[D- $\beta$-Nal-1, D-p-Cl-Phe-2, D-Trp-3, D-Arg-6, Tyr-7, D-Ala-10]-LH-RH, Ac-[D- $\beta$-Nal-1, D-p-Cl-Phe-2, D-Trp-3, D-Arg-6, p-Cl-Phe-7, D-Ala-10]-LH-RH, Ac-[D- $\beta$-Nal-1, D-p-Cl-Phe-2, D-Trp-3, D-Arg-6, p-F-Phe-7, D-Ala-10]-LH-RH, Ac-[D- $\beta$-Na-1, D-p-Cl-Phe-2, D-Trp-3, D-Arg-6, p-Me-Phe-7, D-Ala-10]-LH-RH, Ac-[D- $\beta$-Nal-1, D-p-Cl-Phe-2, D-Trp-3, D-Arg-6, pentafluoro-Phe-7, D-Ala-10]-LH-RH, Ac-[D-$\beta$-Nal-1, D-p-Cl-Phe-2, D-Trp-3, D-Arg-6, Trp-7, D-Ala-10]-LH-RH, Ac-[D-$\beta$-Nal-1, D-p-Cl-Phe-2, D-Trp-3, D-Arg-6, $\beta$-Nal-7, D-Ala-10]-LH-RH, Ac[D- $\beta$-Nal-1, D-p-Cl-Phe-2, D-Trp-3, D-Arg-6, Phe-7, hydroxy-Pro-9, D-Ala-10]-LH-RH, Ac-[D-$\beta$-Nal-1, D-p-Cl-Phe-2, D-Lys-6, Phe-7, D-Ala-10]-LH-RH, and Ac-[D-p-Cl-Phe-1, D-p-Cl-Phe-2, D-Trp-3, D-Arg-6, Phe-7, D-Ala-10]-LH-RH are prepared in similar yields in an analogous fashion by appropriately modifying the above procedure.

Use

When administered to a mammal (e.g., orally, intravenously, parenterally, nasally, or by suppository), the decapeptides are effective in inhibiting the release of LH-RH.

The decapeptides of the invention can be used for the treatment of precocious puberty, hirsutism, acne, amenorrhea (e.g., secondary amenorrhea), endometriosis, and ovarian and mammary cystic diseases. The decapeptides can also be used to regulate human menopausal gonadotropin luteinizing hormone (LH) and follicle-stimulating hormone (FSH) during perimenopausal and postmenopausal periods in women. The decapeptides can also be used as female contraceptives.

The decapeptides can be administered to a patient in a dosage of 10 mcg/kg/day to 1000 mcg/kg/day, preferably 25-250 mcg/kg/day.

Other embodiments are within the following claims.

I claim:

1. A decapeptide of the formula:
Ac-$A^1$-$A^2$-D-Trp-Ser-Tyr-$A^3$-$A^4$-$A^5$-$A^6$-$A^7$-$NH_2$
   wherein each $A^1$ and $A^2$, independently, is D-Trp, D- 62 -Nal, or D-p-X-Phe, wherein X is a halogen or $CH_3$;
   $H^3$ is D- $\beta$-Nal, D-Trp, D-Lys, D-Arg, D-homo-Arg, D-diethyl-homo-Arg, or D-p-X-Phe, wherein X is a halogen or $CH_3$;
   $A^4$ is Phe, Tyr, pentafluoro-Phe, Trp, $\beta$-Nal, or p-X-Phe, wherein X is a halogen;
   $A^5$ is Arg or Lys;
   $A^6$ is Pro or hydroxy-Pro; and
   $A^7$ is Gly or D-Ala;
or a pharmaceutically acceptable salt thereof.

2. The decapeptide of claim 1, wherein $A^1$ is D- $\beta$-Nal; $A^2$ is D-p-Cl-Phe; $A^3$ is D-Arg; $A^5$ is Arg; and $A^7$ is D-Ala; or a pharmaceutically acceptable salt thereof.

3. The decapeptide of claim 2, wherein $A^4$ is Phe and $A^6$ is Pro; or a pharmaceutically acceptable salt thereof.

4. The decapeptide of claim 2, wherein $A^4$ is Tyr and $A^6$ is Pro; or a pharmaceutically acceptable salt thereof.

5. The decapeptide of claim 2, wherein $A^4$ is p-Cl-Phe and $A^6$ is Pro; or a pharmaceutically acceptable salt thereof.

6. The decapeptide of claim 2, wherein $A^4$ is p-F-Phe and $A^6$ is Pro; or a pharmaceutically acceptable salt thereof.

7. The decapeptide of claim 2, wherein $A^4$ is p-ME-Phe and $A^6$ is Pro; or a pharmaceutically acceptable salt thereof.

8. The decapeptide of claim 2, wherein $A^4$ is pentafluoro-Phe and $A^6$ is Pro; or a pharmaceutically acceptable salt thereof.

9. The decapeptide of claim 2, wherein $A^4$ is Trp and $A^6$ is Pro; or a pharmaceutically acceptable salt thereof.

10. The decapeptide of claim 2, wherein $A^4$ is $\beta$-Nal and $A^6$ is Pro; or a pharmaceutically acceptable salt thereof.

11. The decapeptide of claim 2, wherein $A^4$ is Phe and $A^6$ is hydroxy-Pro; or a pharmaceutically acceptable salt thereof.

12. The decapeptide of claim 1, wherein $A^1$ is D-$\beta$-Nal; $A^2$ is D-p-Cl-Phe; $A^3$ is D-Lys; $A^4$ is Phe; $A^5$ is Arg; $A^6$ is Pro; and $A^7$ is D-Ala; or a pharmaceutically acceptable salt thereof.

13. The decapeptide of claim 1, wherein $A^1$ is D-p-Cl-Phe; $A^2$ is D-p-Cl-Phe; $A^3$ is D-Arg; $A^4$ is Phe; $A^5$ is Arg; $A^6$ is Pro; and $A^7$ is D-Ala; or a pharmaceutically acceptable salt thereof.

* * * * *

UNITED STATES PATENT AND TRADEMARK OFFICE
CERTIFICATE OF CORRECTION

PATENT NO. : 4,647,653
DATED : March 3, 1987
INVENTOR(S) : David H. Coy et al.

It is certified that error appears in the above-identified patent and that said Letters Patent is hereby corrected as shown below:

COLUMN 1, LINE 3
As a first sentence and paragraph, insert the paragraph:

--This invention was made in the course of work under a grant or award from the U.S. government; therefore, the U.S. government has rights in the invention.--

Signed and Sealed this

Twenty-fourth Day of December, 1991

Attest:

HARRY F. MANBECK, JR.

Attesting Officer  Commissioner of Patents and Trademarks